United States Patent [19]

Tarzia et al.

[11] 4,211,708
[45] Jul. 8, 1980

[54] AMINOPYRROLE DERIVATIVES

[75] Inventors: Giorgio Tarzia, Rome; Gianbattista Panzone, Milan, both of Italy

[73] Assignee: Gruppo Lepetit S.p.A., Milan, Italy

[21] Appl. No.: 960,385

[22] Filed: Nov. 13, 1978

Related U.S. Application Data

[60] Division of Ser. No. 750,759, Dec. 15, 1976, Pat. No. 4,140,696, which is a continuation-in-part of Ser. No. 716,749, Aug. 23, 1976, abandoned, which is a continuation-in-part of Ser. No. 492,564, Jul. 29, 1974, abandoned.

[30] Foreign Application Priority Data

Aug. 22, 1973 [GB] United Kingdom .............. 39790/73

[51] Int. Cl.$^2$ ........................................... C07D 207/44
[52] U.S. Cl. ........................... 260/326.46; 260/326.2; 260/326.47; 260/326.5 J; 542/414
[58] Field of Search .................... 260/326.46, 326.47, 260/326.2; 542/414

[56] References Cited

U.S. PATENT DOCUMENTS 4,140,696   2/1979   Tarzia et al. ................... 260/326.5 J Primary Examiner—Jose Tovar

[57] ABSTRACT

Pharmacologically-active aminopyrrole derivatives of the formula

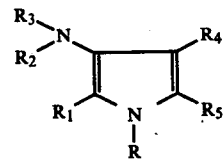

wherein:
R is selected from hydrogen, ($C_{1-4}$)alkyl, benzyl and chlorobenzyl;
$R_1$ is selected from hydrogen, ($C_{1-4}$)alkyl, phenyl and phenyl substituted by a radical selected from methyl, ethyl, methoxy, ethoxy, benzyloxy, fluoro, chloro and bromo;
$R_2$ and $R_3$ individually represent hydrogen or ($C_{1-4}$)alkyl or, taken together, represent an isopropylidene, a benzylidene or a chlorobenzylidene radical;
$R_4$ is selected from ($C_{2-4}$)alkanoyl; carbo($C_{1-3}$)alkoxy; benzoyl, benzoyl substituted by a radical selected from chloro, methoxy or ethoxy; carbamoyl, methylcarbamoyl and phenyl carbamoyl;
$R_5$ is selected from hydrogen, ($C_{1-4}$)alkyl, carbo($C_{1-3}$)alkoxy, carbomethoxymethyl, carbethoxymethyl, trifluoromethyl and carbamoyl, with the proviso that when R is hydrogen, $R_1$ and $R_5$ are methyl and $R_4$ is carbethoxy, $R_2$ and $R_3$ cannot simultaneously represent hydrogen;
and a salt thereof with a pharmaceutically-acceptable acid.

The compounds have anti-inflammatory and CNS-depressant utility. They are also useful as analgesics and antipyretics and display a very low degree of antiulcerogenic activity.

8 Claims, No Drawings

AMINOPYRROLE DERIVATIVES

CROSS REFERENCE TO RELATED APPLICATIONS

This is a division, of application Ser. No. 750,759, filed Dec. 15, 1976, now U.S. Pat. No. 4,140,696 issued Feb. 20, 1979, which is a continuation-in-part of U.S. patent application, Ser. No. 716,749, filed Aug. 23, 1976 the latter being a continuation-in-part of U.S. patent application Ser. No. 492,564, filed July 29, 1974, last two abandoned.

SUMMARY OF THE INVENTION

The present invention concerns aminopyrrole derivatives of the formula

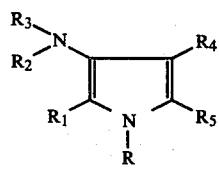

wherein:
- R is selected from hydrogen; $(C_{1-4})$alkyl, e.g. methyl, ethyl, propyl, isopropyl, butyl, isobutyl or tert-butyl; benzyl and chlorobenzyl;
- $R_1$ is selected from hydrogen, $(C_{1-4})$alkyl as above defined, phenyl and phenyl substituted by a radical selected from methyl, ethyl, methoxy, ethoxy, benzyloxy, fluoro, chloro and bromo;
- $R_2$ and $R_3$ individually represent hydrogen or $(C_{1-4})$alkyl as above defind or, taken together, represent an isopropylidene, a benzylidene or a chlorobenzylidene radical;
- $R_4$ is selected from $(C_{2-4})$alkanoyl, e.g., acetyl, propionyl, butyryl or isobutyryl; carbo$(C_{1-3})$alkoxy, e.g., carbomethoxy, carbethoxy or carbopropoxy; benzoyl, benzoyl substituted by a radical selected from chloro methoxy or ethoxy; carbamoyl, methylcarbamoyl and phenylcarbamoyl;
- $R_5$ is selected from hydrogen, $(C_{1-4})$alkyl as above defined carbo$(C_{1-3})$alkoxy as above defined, carbomethoxymethyl, carbethoxymethyl, trifluoromethyl and carbamoyl;

with the proviso that when R is hydrogen, $R_1$ and $R_5$ are methyl and $R_4$ is carbethoxy, $R_2$ and $R_3$ cannot simultaneously represent hydrogen;

and a salt thereof with a pharmaceutically-acceptable acid.

The compounds have anti-inflammatory and CNS-depressant utility. They are also useful as analgesics and antipyretics and display a very low degree of anti-ulcerogenic activity.

A preferred group of compounds comprises those compounds of Formula I wherein R is hydrogen, $(C_{1-4})$alkyl as above defined or chlorobenzyl; $R_1$ is hydrogen, phenyl or phenyl substituted by a radical selected from methyl, ethyl, methoxy, ethoxy, fluoro and chloro; $R_2$ and $R_3$ are both hydrogen or methyl or, taken together, benzylidene or chlorobenzylidene; $R_4$ is $(C_{2-4})$alkanoyl as above defined; carbo$(C_{1-3})$alkoxy as above defined; benzoyl; benzoyl substituted by methoxy or ethoxy; carbamoyl, methylcarbamoyl or phenylcarbamoyl; and $R_5$ is hydrogen, $(C_{1-4})$alkyl as above defined or carbamoyl; and a salt thereof with a pharmaceutically-acceptable acid.

A most preferred group of compounds comprises those compounds of Formula I wherein R is hydrogen, methyl or chlorobenzyl; $R_1$ is phenyl or phenyl substituted by a radical selected from methyl, methoxy, fluoro and chloro; $R_2$ and $R_3$ individually are both hydrogen or methyl or, taken together, are benzylidene or chlorobenzylidene; $R_4$ is $(C_{2-4})$alkanoyl as above defined; carbethoxy; benzoyl; methoxybenzoyl; or methylcarbamoyl; and $R_5$ is hydrogen, methyl, propyl or carbamoyl; and a salt thereof with a pharmaceutically-acceptable acid.

The compounds of the invention are prepared by reacting an α-aminonitrile of the formula $$NH_2CH(R_1)CN \qquad II$$

or an acid addition salt thereof, wherein $R_1$ has the meaning given above, with a compound of the formual:

$$X(R_4)R_5 \qquad III$$

wherein $R_4$ and $R_5$ have the significance given above and X represents a $-C\equiv C-$ group or a

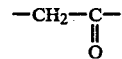

group wherein the $CH_2$-portion is linked to the substituent $R_4$. It is understandable to any person who is skilled in the art that substances which have chemical properties similar to those displayed by β-dicarbonyl compounds or by acetylenecarbonyl compounds may advantageously be employed, such as, for instance, substances of Formula III in which X is $-CH=C(hal)-$, wherein hal represents a halogen atom, preferably chlorine and the carbon atoms bearing the halogen atom is linked to the radical $R_5$.

The starting aminonitriles are prepared following substantially the method described by Steiger in "Organic Syntheses", 22, 13, 1942 and 22, 23, 1942. The compounds of Formula III either are commercially available products or are obtained through obvious modifications of commercially-available products.

The reaction generally proceeds with the formation of an intermediate open-chain compound representable by following Formula IV or its tautomeric iminic form:

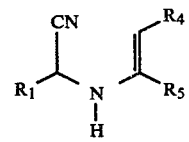

which, if desired, may be isolated, purified and characterized by means of common analytical procedures before cyclization. However, it may also be used as a raw material for the subsequent cyclization step without affecting the final yields.

According to a preferred mode of carrying out the process of the invention, the reactants II and III are contacted in substantially equimolecular amounts in the presence of an anhydrous organic solvent which is preferably selected from benzene, dioxane, tetrahydrofuran, lower alkanols and analogs. A small amount of p-toluenesulfonic acid as the catalyst may be added and the mixture is refluxed for a time varying from about 2 to about 28 hours. The intermediate compound of Formula IV which forms may be isolated and characterized, if desired, or employed as such for the subsequent cyclization step, which is carried out in the presence of a basic catalyst, advantageously selected from carbonates, hydroxides, alkoxides, hydrides and amides of the metals of the I and II group of the periodic table of the elements. Also in this case, the reaction is carried out in the presence of a solvent which is preferably selected from the anhydrous lower alkanols having a maximum of four carbon atoms.

The cyclization usually takes place at room temperature, but sometimes it is necessary to heat or to reflux the reaction mixture in order to speed up the cyclization reaction which is completed within an interval of time ranging from about 1 to about 30 hours.

In some instances, it has been observed that when X represents a —C≡C—moiety, the formation of the aminopyrrole nucleus may take place in one reaction step only. In this case, the aminonitrile of Formula II, or an acid addition salt thereof, and the compound of Formula III wherein X is a —C≡C—group, are mixed together in substantially equimolecular ratios, in the presence of an organic solvent such as, for instance, an anhydrous $(C_{1-4})$alkanol, chloroform, tetrahydrofuran, benzene and analogs and an alkali or alkaline earth metal carbonate or hydroxide as the catalyst and the resulting mixture is refluxed for about 3–5 hours.

Pursuant to the outlined procedures, a compound of Formula I is obtained wherein R, $R_2$ and $R_3$ represent hydrogen. It is recovered from the reaction mixture as the free base or in the form of a salt of a pharmaceutically-acceptable acid, following techniques which are entirely familiar to a skilled chemist. These techniques comprise removing the solvent from the reaction mixture by evaporation, taking up the residue with a solvent, again evaporating the solvent and purifying the obtained solid, liquid or oily substance by recrystallization, fractional distillation, or distillation under reduced pressure.

If a crystalline solid directly results from the reaction, it is recovered simply by filtration, and, if necessary, is purified by recrystallization. Recrystallization solvents are preferably selected from $C_1$-$C_4$ lower alkanols, diethyl ether or mixtures thereof.

By a salt of a pharmaceutically-acceptable acid is meant the hydrochloride, hydrobromide, hydroiodide, sulfate, phosphate, benzoate, oxalate, acetate, methanesulfonate, cyclohexylsulfonate, and analogs thereof. Such a salt is easily obtained by treating a compound as the free base with a predetermined pharmaceutically-acceptable acid. In turn, it is possible to regenerate the free base from the corresponding acid salt by reaction with at least one equimolecular amount of a basic agent.

As illustrated above, the condensation between the compounds of Formulas II and III affords a compound of Formula I wherein R, $R_2$ and $R_3$ represent hydrogen. When R, $R_2$ and $R_3$ are desired to be different from hydrogen, the corresponding radicals are introduced according to common chemical procedures. As an example, the compounds wherein $R_2$ and/or $R_3$ are $(C_{1-4})$alkyl are prepared by reaction with $(C_{1-4})$alkyl halides or $(C_{1-4})$alkyl sulfates. On the other hand, compounds where $R_2$ and/or $R_3$ are methyl can also be prepared by reaction with a mixture of formic acid and formaldehyde.

Substances wherein $R_2$ and $R_3$ taken together represent isopropylidene, benzylidene or chlorobenzylidene are easily prepared according to known reactions for obtaining Schiff's bases from amines and carbonyl compounds.

Finally, the compounds of Formula I wherein $R_4$ or $R_5$ or both represent a carbamoyl group can be prepared by saturating with ammonia an alcoholic solution of a corresponding compound of Formula I wherein $R_4$ or $R_5$ or both represent a carbo($C_{1-3}$)alkoxy group.

The substitution on the ring nitrogen atom generally does not take place under the above reaction conditions for introducing the radicals $R_2$ and $R_3$ onto the aminic nitrogen atom or modifying the groups $R_4$ and/or $R_5$. A convenient method for introducing the desired substituents of Formula I on the nuclear nitrogen atom of the pyrrole ring involves reaction of a predetermined compound of Formula I wherein R is hydrogen with a selected $(C_{1-4})$alkyl, benzyl or chlorobenzyl halide in the presence of a strong basic agent, preferably an alkali metal or alkali metal hydride, in an inert organic solvent, such as, for instance, dimethylformamide, under a nitrogen atmosphere. The reaction is carried out at room temperature. The desired aminopyrrole substituted at position 1 is then isolated from the reaction mixture in good yield.

It is understandable that, if this reaction is carried out on a substrate wherein $R_2$ or $R_3$ or both represent hydrogen, an analogous substitution can also occur on the aminic nitrogen. This means that, in the obtained compound, the amino group at the 3-position can contemporaneously be substituted, for instance, by one or two $(C_{1-4})$alkyl groups. However, if a compound of Formula I wherein $R_2$ and $R_3$ are hydrogen which is substituted at the nuclear nitrogen atom is desired, it is necessary to protect the amino group at the 3-position, e.g., by reaction with a carbonyl compound or an alkylsulfonyl or benzenesulfonyl halide to prepare the corresponding Schiff's base or the alkylsulfonyl or benzenesulfonylamino derivative, respectively. Then the substitution at the 1-position is carried out as outlined above and an acidic hydrolytic cleavage of the protecting group affords the desired compounds wherein $R_2$ and/or $R_3$ represent hydrogen.

Other obvious routes useful for introducing appropriate substituents at the desired positions or for modifying a pre-existing radical into another falling within the given meanings, are useful for providing compounds within the scope of the invention.

The compounds of the invention possess pharmacological utility. More particularly, they possess a remarkable anti-inflammatory, analgesic and CNS-depressant utility.

An aspect of the anti-inflammatory utility was evidenced by means of the carrageenin-induced edema test in rats, which was performed according to the methodology described by C. A. Winter et al., Proc. Soc. Exptl. Biol. Med., 111, 544, 1962. In representative experiments, it was found that the compounds of Examples 1, 2, 3, 6, 13, 14, 15, 17, 19, 20, 21, 24, 26, 29, 31, 34, 35, 43, 45, 46, 49a, 49b, 53, 54, and 55 caused a percent decrease of the induced edema varying from about 35 to about 80 when administered at a dose level comprised between 1/50 and 1/5 of their $LD_{50}$ values. It is also to be noted that the toxicities of the aminopyrrole derivatives which are the object of the present invention are very low; with few exceptions, their LD$_{50}$ values are always higher than 1000 mg/kg p.o. in mice. Toxicities were determined according to the procedure described by Lichtfield and Wilcoxon, J. Pharm. Exp. Ther., 96, 99, 1949.

The following Table summarizes the aforementioned anti-inflammatory action and LD$_{50}$ values.

TABLE I

| Compound of Example | LD$_{50}$ mg/kg p.o., mice | Dose mg/kg p.o., rats | % Decrease of the induced edema |
|---|---|---|---|
| 1 | >1000* | 5 | 23.4 |
|  |  | 10 | 32.5 |
|  |  | 20 | 39.0 |
|  |  | 50 | 43.8 |
|  |  | 100 | 58.9 |
|  |  | 200 | 76.6 |
| 2 | >1000 | 100 | 36.5 |
|  |  | 200 | 44.3 |
| 3 | >1000 | 100 | 40.6 |
|  |  | 200 | 53.9 |
| 6 | >1000 | 100 | 25.7 |
|  |  | 200 | 35.0 |
| 13 | >1000 | 5 | 23.2 |
|  |  | 10 | 31.9 |
|  |  | 20 | 43.5 |
|  |  | 50 | 50.7 |
|  |  | 100 | 69.6 |
|  |  | 200 | 75.4 |
| 14 | >1000 | 5 | 23.0 |
|  |  | 10 | 31.1 |
|  |  | 20 | 35.1 |
|  |  | 50 | 41.9 |
|  |  | 100 | 55.4 |
|  |  | 200 | 67.6 |
| 15 | >1000 | 50 | 29.6 |
|  |  | 100 | 40.8 |
|  |  | 200 | 58.3 |
| 17 | >1000 | 100 | 35.4 |
|  |  | 200 | 47.9 |
| 19 | 500 | 50 | 24.3 |
|  |  | 100 | 45.9 |
| 20 | >1000 | 50 | 24.2 |
|  |  | 100 | 37.3 |
|  |  | 200 | 44.9 |
| 21 | 500 | 20 | 25.3 |
|  |  | 50 | 36.0 |
|  |  | 100 | 43.0 |
| 24 | 500 | 20 | 20.6 |
|  |  | 50 | 32.3 |
|  |  | 100 | 42.2 |
| 26 | >1000 | 20 | 29.2 |
|  |  | 50 | 43.1 |
|  |  | 100 | 58.5 |
|  |  | 200 | 71.0 |
| 29 | >1000 | 50 | 26.4 |
|  |  | 100 | 33.8 |
|  |  | 200 | 42.6 |
| 31 | ~1000** | 50 | 26.1 |
|  |  | 100 | 34.8 |
|  |  | 200 | 42.0 |
| 34 | ~1000 | 50 | 39.1 |
|  |  | 100 | 50.0 |
|  |  | 200 | 61.3 |
| 35 | 500 | 50 | 32.4 |
|  |  | 100 | 42.0 |
| 43 | >1000 | 100 | 25.3 |
|  |  | 200 | 45.6 |
| 45 | >1000 | 50 | 23.9 |
|  |  | 100 | 47.9 |
|  |  | 200 | 68.2 |
| 46 | >1000 | 20 | 23.9 |
|  |  | 50 | 35.2 |
|  |  | 100 | 47.9 |
|  |  | 200 | 69.0 |
| 49a | >1000 | 100 | 31.0 |
|  |  | 200 | 53.1 |
| 49b | >1000 | 50 | 11.0 |
|  |  | 100 | 34.3 |
|  |  | 200 | 52.7 |
| 53 | >1000 | 100 | 30.0 |
| 54 | >1000 | 200 | 37.1 |
|  |  | 100 | 38.0 |
|  |  | 200 | 47.6 |
| 55 | 1000 | 50 | 27.1 |
|  |  | 100 | 41.4 |
|  |  | 200 | 56.3 |

*> higher than
**~ about

The compounds of the invention are also useful an antipyretics and analgesics. The antipyretic activity was found to be about two to about ten times that of aspirin, while the analgesic activity was found to be about four times that of aspirin. Moreover, the compounds of the invention possess a very low degree of ulcerogenic activity. The analgesic activity was evaluated according to the procedure of L. O. Randall and J. J. Selitto, Arch. Int. Phamacodyn., No. 4, CXI, page 409, 1957. The antipyretic activity was investigated according to the procedure of R. H. Buller et al., J. Pharma. Pharmacol., 9, 128, 1957, whereas the ulcerogenic action was determined according to the procedure of Thuillier et al., Chim. Therap. 3, 53, 1968.

As stated above, the aminopyrrole derivatives described in the present invention also possess CNS-depressant utility. This characteristic was investigated according to the general method proposed by S. Irwin, Psychopharmacologia (Berl.), 13, 222, 1968. It was found that of the compounds which showed particularly effective anti-inflammatory properties such as, for instance, the compounds of Examples 1 and 15, were also endowed with a good degree of sedative and myorelaxing activity. This is undoubtedly another very favorable characteristic of the inventive compounds, as a certain sedative and myorelaxing effect is useful in patients affected by severe inflammatory disease.

While the preferred routes of administration are oral and rectal, parenteral administration can also be employed. For oral administration, the compounds are compounded into pharmaceutical dosage forms, such as, for instance, tablets, capsules, elixirs, solutions and the like.

The dosage unit may contain usual excipients, e.g., starch, gums, fatty acids, alcohols, sugars, etc. For rectal administration, the compounds are administered in the form of suppositories, admixed with conventional vehicles, such as, for example, cocoa butter, wax, spermaceti or polyoxyethyleneglycols and their derivatives. The dosage range is from about 0.05 to about 2.00 g/kg per day, preferably administered in divided doses. Accordingly, the present invention provides a therapeutic composition containing as the active ingredient a compound of the invention together with a pharmaceutically-acceptable carrier.

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

EXAMPLE 1:
4-Acetyl-3-amino-5-methyl-2-phenylpyrrole hydrochloride (a) A solution of 2 g (0.015 mole) of 2-amino-2-phenylacetonitrile and 1.4 g (0.014 mole) of acetylacetone in 30 ml of anhydrous benzene is refluxed for two hours on an oil bath in the presence of 100 mg of p-toluenesulfonic acid. After cooling, the reaction mixture is filtered, then the solvent is evaporated off to give an oily residue which is distilled under reduced pressure. The so-obtained intermediate open-chain compound boils at 150° C./0.1 mm Hg.

(b) 0.40 Gram of sodium is dissolved in 15 ml of anhydrous ethanol, then a solution of 2.5 g of the compound prepared as in preceding (a) in anhydrous ethanol is added dropwise and the mixture is allowed to stand at room temperature for four hours. After bubbling dry hydrogen chloride in the ethanol solution, a precipitate forms which is recovered by filtration and recrystallized from ethanol/diethyl ether. Yield 2.0 g of the title compound. M.p. 242° C. (with decomposition). The free base is obtained by extraction with ethyl acetate of an aqueous solution of the hydrochloride and alkalinized with 5% sodium hydroxide. M.p. 220° C. (from methanol).

EXAMPLE 2:
3-Amino-4-carbethoxy-5-methyl-2-phenylpyrrole hydrochloride (a) A solution of 6 g (0.042 mole) of 2-amino-2-phenylacetonitrile and 5 g (0.042 mole) of ethyl acetoacetate in 30 ml of anhydrous benzene is refluxed for four hours on an oil bath in the presence of 100 mg of p-toluenesulfonic acid. After cooling, the reaction mixture is filtered, then the solvent is evaporated off to give an oily residue, which is distilled under reduced pressure. The open-chain intermediate compound which is obtained has a b.p. 140° C./0.05 mm Hg.

(b) 0.80 Gram of sodium is dissolved in 15 ml of anhydrous ethanol, then a solution of 5 g of the above compound in 35 ml of anhydrous ethanol is added dropwise and the mixture is allowed to stand at room temperature for four hours. After bubbling dry hydrogen chloride in the ethanol solution, a precipitate readily forms, which is filtered and recrystallized from a mixture of ethanol and diethyl ether. Yield 4 g. M.p. 249°–252° C. (from ethanol/ethyl ether).

EXAMPLES 3–42

The following compounds are prepared pursuant to the two-step procedure described in Example 1, starting from the appropriate compounds of Formulas II and III and using alkali metal alkoxides or carbonates as the cyclizing basic catalysts. When the open-chain intermediate compounds are isolated and characterized, their chemico-physical properties are reported, otherwise these intermediates are directly cyclized to the end compounds.

EXAMPLE 3:
3-Amino-4-benzoyl-5-methyl-2-phenylpyrrole hydrochloride

Starting from 2-amino-2-phenylacetonitrile and benzoylacetone, and open-chain intermediate compound is obtained, melting at 134°–35° C. (from diethyl ether/hexane). The title compound is obtained in a 60% overall yield. M.p. 285°–290° C. (from methanol/diethyl ether). The free base melts at 203°–5° C. (from methanol).

EXAMPLE 4: 3-Amino-4-benzoyl-2-phenylpyrrole hydrochloride

The open-chain intermediate compound, melting at 88°–90° C. (from hexane), is prepared from 2-amino-2-phenylacetonitrile and benzoyl acetaldehyde. The title compound is obtained in a 47% overall yield; m.p. 272°–74° C. (from ethanol).

EXAMPLE 5:
4-Acetyl-3-amino-2-ethyl-5-methylpyrrole hydrochloride

Starting from 2-aminobutyronitrile and acetylacetone, the open-chain intermediate compound is obtained, boiling at 100° C./0.02 mm Hg. The title product is obtained in a 49% overall yield, m.p. 245°–48° C. (from ethanol/diethyl ether). The free base melts at 219°–21° C. (from methanol).

EXAMPLE 6: 3-Amino-4-carbethoxy-2-phenylpyrrole hydrochloride

The title compound is obtained in a 45% overall yield from 2-amino-2-phenylacetonitrile and ethyl propynoate; m.p. 244°–45° C. (from ethanol/diethyl ether).

EXAMPLE 7:
3-Amino-4-benzoyl-5-carbethoxy-2-phenylpyrrole hydrochloride

The title compound is obtained in a 48% overall yield from 2-amino-2-phenylacetonitrile and benzoyl pyruvic acid ethyl ester; m.p. 218°–9° C. (from ethanol/diethyl ether).

EXAMPLE 8: 4-Acetyl-3-amino-2-phenylpyrrole hydrochloride

Starting from 2-amino-2-phenylacetonitrile and acetylacetaldehyde, the open-chain intermediate compound is obtained, boiling at 140° C./0.05 mm Hg. The title compound is obtained in an overall yield of 56%. It does not melt up to 335° C.

EXAMPLE 9:
4-Acetyl-3-amino-2-(p-methoxyphenyl)pyrrole

Starting from 2-amino-2-(p-methoxyphenyl)acetonitrile and acetylacetaldehyde, the open-chain intermediate product is prepared, boiling at 180° C./0.03 mm Hg. Overall yield of the title compound: 44%, m.p. 198°–200° C. (from diethyl ether).

EXAMPLE 10: 3-Amino-4-benzoyl-5-methylpyrrole hydrochloride

Starting from aminoacetonitrile and benzoylacetone, the open-chain intermediate compound is obtained, melting at 111°–12° C. (from diethyl ether). Overall yield of the title compound: 52%, m.p. 225°–270° C. (from ethanol/diethyl ether).

EXAMPLE 11: 4-Acetyl-3-amino-5-methylpyrrole hydrochloride

Starting from aminoacetonitrile and acetylacetone, the open-chain intermediate compound is obtained, melting at 106°–8° C. (from diethyl ether). The title compound is obtained in a 64% overall yield, m.p. 211°–12° C. (from ethanol).

EXAMPLE 12:
3-Amino-4-carbethoxy-5-carbethoxymethyl-2-phenylpyrrole hydrochloride The title compound is obtained in a 42% overall yield from 2-amino-2-phenylacetonitrile and 1,3-dicarbethoxyacetone; m.p. 232°–36° C. (from diethyl ether/ethanol).

EXAMPLE 13:
4-Acetyl-3-amino-5-methyl-2-(p-tolyl)pyrrole

The title compound is obtained in a 94% overall yield from 2-amino-2-(p-tolyl)acetonitrile and acetylacetone; m.p. 232°–4° C. (from ethanol/diethyl ether).

EXAMPLE 14:
4-Acetyl-3-amino-2-(p-methoxyphenyl)-5-methylpyrrole

The title compound is prepared in a 92% overall yield from 2-amino-2-(p-methoxyphenyl)acetonitrile and acetylacetone; m.p. 222°–23° C. (from ethanol).

EXAMPLE 15:
3-Amino-4-carbethoxy-5-methyl-2-(p-tolyl)pyrrole hydrochloride Starting from 2-amino-2-(p-tolyl)acetonitrile and ethyl acetoacetate, the open-chain intermediate compound, boiling at 160° C./0.05 mm Hg, is obtained. Overall yield of the title product: 88%, m.p. 266°–68° C. (from methanol).

EXAMPLE 16:
3-Amino-4-carbethoxy-2-phenyl-5-trifluoromethylpyrrole hydrochloride The title compound is obtained in a 52% overall yield from 2-amino-2-phenylacetonitrile and trifluoroacetyl ethyl acetate; m.p. 203°–5° C. (from ethanol).

EXAMPLE 17:
4-Acetyl-3-amino-2-(p-fluorophenyl)-5-methylpyrrole

Starting from 2-amino-2-(p-fluorophenyl)acetonitrile and acetylacetone, the open-chain intermediate compound is obtained; b.p. 150° C./0.3 mm Hg. Overall yield of the title compound: 47%, m.p. 211°–12° C. (from ethanol).

EXAMPLE 18:
3-Amino-4-carbethoxy-2-(p-fluorophenyl)-5-methylpyrrole hydrochloride The open-chain intermediate compound is obtained from 2-amino-2-(p-fluorophenyl)acetonitrile and ethyl acetoacetate, b.p. 220° C./0.2 mm Hg. The title product is obtained in a 53% overall yield, m.p. 258°–60° C. (from ethanol/diethyl ether).

EXAMPLE 19:
3-Amino-4-carbethoxy-5-methylpyrrole hydrochloride

The open-chain intermediate compound is obtained from aminoacetonitrile and ethyl acetoacetate, m.p. 90°–98° C. (from methanol). The title compound is obtained in a 44% overall yield, m.p. 211°–14° C. (from methanol).

EXAMPLE 20:
3-Amino-4-isobutyryl-5-methyl-2-phenylpyrrole

The open-chain intermediate compound is obtained from 2-amino-2-phenylacetonitrile and 5-methylhexane-2,4-dione, b.p. 150° C./0.3 mm Hg. Overall yield of the title compound: 64%, m.p. 180°–83° C. (from methanol/diethyl ether).

EXAMPLE 21:
3-Amino-5-methyl-2-phenyl-4-propionylpyrrole

Starting from 2-amino-2-phenylacetonitrile and hexane-2,4-dione, the open-chain intermediate compound is obtained, b.p. 160° C./0.3 mm Hg. The title compound is obtained in an overall yield of 53%, m.p. 166°–168° C. (from methanol).

EXAMPLE 22:
4-Acetyl-3-amino-5-methyl-2-(m-tolyl)pyrrole

Starting from 2-amino-2-(m-tolyl)acetonitrile and acetylacetone, the open-chain intermediate compound is obtained, b.p. 170° C./0.02 mm Hg. The title compound is obtained in a 59% overall yield, m.p. 195°–7° C. (from ethanol).

EXAMPLE 23:
4-Acetyl-3-amino-2-ethyl-5-methylpyrrole hydrochloride

The title compound is obtained in a 73% overall yield from 2-aminobutyronitrile and acetylacetone, m.p. 245°–48° C. (from methanol).

EXAMPLE 24:
3-Amino-4-(p-methoxybenzoyl)-5-methyl-2-phenylpyrrole

The title compound is obtained in a 43% overall yield from 2-amino-2-phenylacetonitrile and (p-methoxybenzoyl)acetone, m.p. 219°–21° C. (from ethanol).

EXAMPLE 25:
4-Acetyl-3-amino-2-(p-benzyloxyphenyl)-5-methylpyrrole

The title compound is obtained in a 51% overall yield from 2-amino-2-(p-benzyloxyphenyl)acetonitrile and acetylacetone, m.p. 245°–50° C. (from ethanol).

EXAMPLE 26:
4-Acetyl-3-amino-2-(p-chlorophenyl)-5-methylpyrrole

The title compound is obtained in a 67% overall yield starting from 2-amino-2-(p-chlorophenyl)acetonitrile and acetylacetone, m.p. 205°–8° C. (from ethanol).

EXAMPLE 27:
3-Amino-4-carbethoxy-2-(p-methoxyphenyl)-5-methylpyrrole hydrochloride The title compound is obtained in a 44% overall yield from 2-amino-2-(p-methoxyphenyl)acetonitrile and ethyl acetoacetate, m.p. 234°–36° C. (from methanol).

EXAMPLE 28:
3-Amino-4-benzoyl-2-(p-fluorophenyl)-5-methylpyrrole

Starting from 2-amino-2-(p-fluorophenyl)acetonitrile and benzoyl acetone, the open-chain intermediate compound is obtained, b.p. 120° C./0.2 mm Hg. The title compound is obtained in a 66% overall yield, m.p. 209°–10° C. (from ethanol/diethyl ether).

EXAMPLE 29:
4-Acetyl-3-amino-2-(o-tolyl)-5-methylpyrrole

Starting from 2-amino-2-(o-tolyl)acetonitrile and acetylacetone, the open-chain intermediate compound is obtained, b.p. 120° C./0.2 mm Hg. The title compound is obtained in a 77% overall yield, m.p. 258° C. (from methanol).

EXAMPLE 30:
3-Amino-4-carbomethoxy-5-carbomethoxymethyl-2-phenylpyrrole hydrochloride The title product is obtained in a 48% overall yield starting from 2-amino-2-phenylacetonitrile and 1,3-(dicarbomethoxy)acetone, m.p. 210°–13° C. (from methanol.

EXAMPLE 31:
3-Amino-5-methyl-4-methylcarbamoyl-2-phenylpyrrole hydrochloride The title compound is obtained in a 55% overall yield starting from 2-amino-2-phenylacetonitrile and α-acetyl-N-methylacetamide, m.p. 247°–50° C. (from ethanol).

EXAMPLE 32:
3-Amino-4-(o-chlorobenzoyl)-5-methyl-2-phenylpyrrole

The title compound is obtained in a 51% overall yield, starting from 2-amino-2-phenylacetonitrile and o-chlorobenzoylacetone, m.p. 214°–216° C. (from ethanol).

EXAMPLE 33:
3-Amino-4-carbamoyl-5-methyl-2-phenylpyrrole hydrochloride

Starting from 2-amino-2-phenylacetonitrile and α-acetylacetamide, the open-chain intermediate compound is obtained, m.p. 128°–30° C. (from diethyl ether). The title compound is obtained in a 49% overall yield, m.p. 307°–9° C. (from methanol).

EXAMPLE 34:
3-Amino-4-butyryl-2-phenyl-5-propylpyrrole hydrochloride

The title compound is obtained in a 60% overall yield, starting from 2-amino-2-phenylacetonitrile and nonane-4,6-dione, m.p. 228°–30° C. with decomposition (from methanol/diethyl ether).

EXAMPLE 35:
3-Amino-4-butyryl-5-methyl-2-phenylpyrrole hydrochloride

The title compound is obtained in a 48% yield from 2-amino-2-phenyl-acetonitrile and heptane-2,4-dione, m.p. 240°–45° C. with decomposition (from methanol/diethyl ether).

EXAMPLE 36:
3-Amino-4,5-dicarbomethoxy-2-(p-chlorophenyl)pyrrole hydrochloride Starting from 2-amino-2-(p-chlorophenyl)acetonitrile and dicarbomethoxyacetylene, the open-chain intermediate compound is obtained, m.p. 74°–76° C. (from diethyl ether). The title compound is obtained in a 48% overall yield, m.p. 216°–8° C. (from methanol/diethyl ether).

EXAMPLE 37:
3-Amino-4,5-dicarbomethoxy-2-(p-tolyl)pyrrole hydrochloride

Starting from 2-amino-2-(p-tolyl)acetonitrile and dicarbomethoxyacetylene, the open-chain intermediate compound is obtained, m.p. 76°–77° C. (from diethyl ether/hexane). The title compound is obtained in a 70% overall yield, m.p. 193°–95° C. (from methanol/diethyl ether).

EXAMPLE 38:
3-Amino-4,5-dicarbethoxy-2-phenylpyrrole hydrochloride

Starting from 2-amino-2-phenylacetonitrile and dicarbethoxyacetylene, the open-chain intermediate compound is obtained, b.p. 140° C./0.03 mm Hg. The title compound is obtained in a 78% overall yield, m.p. 193°–96° C. from ethanol/diethyl ether).

EXAMPLE 39:
3-Amino-4,5-dicarbomethoxy-2-(p-methoxyphenyl)-pyrrole hydrochloride Starting from 2-amino-2-(p-methoxyphenyl)acetonitrile and dicarbomethoxyacetylene, the open-chain intermediate compound is obtained, m.p. 86°–88° C. (from hexane). The title compound is obtained in a 63% overall yield, m.p. 195°–97° C. (from methanol/diethyl ether).

EXAMPLE 40:
3-Amino-4,5-dicarbomethoxy-2-ethylpyrrole hydrochloride

The title compound is obtained in a 66% overall yield from 2-aminobutyronitrile and dicarbomethoxyacetylene, m.p. 209°–10° C. (from diethyl ether/methanol).

EXAMPLE 41:
3-Amino-4,5-dicarbomethoxy-2-phenylpyrrole hydrochloride

The title substance is obtained in a 39% overall yield from 2-amino-2-phenylacetonitrile and dicarbomethoxyacetylene, m.p. 205°–7° C. (from methanol/diethyl ether). The free base melts at 142°–43° C. (from diethyl ether).

EXAMPLE 42:
3-Amino-5-methyl-2-phenyl-4-phenylcarbamoylpyrrole

This compound is prepared starting from 2-amino-2-phenylacetonitrile and α-acetyl-N-phenyl-acetamide, and is obtained with a 73% overall yield, m.p. 271°–73° C. (from ethanol).

EXAMPLE 43:
4-Acetyl-3-dimethylamino-5-methyl-2-phenylpyrrole

A solution of 5 g (0.0234 mole) of the compound of Example 1 in 175 ml of methanol and 75 ml of water is heated to 40° C., then 6 g (0.0475 mole) of dimethyl sulfate and 6 g of potassium carbonate are added. The resulting mixture is kept at 40° C. for two hours then, after cooling and diluting with water, is extracted with ethyl acetate. The organic phase is evaporated and the residue is crystallized from dilute methanol; yield 3.87 g, 68%, m.p. 153°–55° C.

EXAMPLE 44:
4-Benzoyl-3-isopropylamino-5-methyl-2-phenylpyrrole

The title compound is prepared by reacting equimolecular amounts of the compound of Example 3 and isopropyl bromide at room temperature, yield 31%, m.p. 132°–36° C. (from hexane).

EXAMPLE 45:
4-Acetyl-3-(p-chlorobenzylideneamino)-5-methyl-2-phenylpyrrole

A solution of 5.0 g (0.0234 mole) of the compound of Example 1 in 200 ml of ethanol is added to a solution of 5.0 g (0.0358 mole) of p-chlorobenzaldehyde in 100 ml of ethanol at 45°–50° C., then the resulting mixture is refluxed for about four hours. After cooling, the reaction mixture is poured into 1200 ml of water saturated with sodium chloride. A precipitate forms which is recovered by filtration and recrystallized from ethanol/water; yield 9.5 g of the title compound, m.p. 214°–15° C.

EXAMPLES 46–48

The following compounds were prepared according to the procedure described in Example 45:

EXAMPLE 46:
4-Acetyl-3-benzylideneamino-5-methyl-2-phenylpyrrole

From the compound of Example 1 and benzaldehyde, yield 87%, m.p. 173°–76° C. (from methanol).

EXAMPLE 47:
4-Carbamoyl-3-isopropylideneamino-5-methyl-2-phenylpyrrole

From the compound of Example 33 and acetone, yield 82%, m.p. 221°–23° C. (from ethanol/hexane).

EXAMPLE 48:
3-Benzylideneamino-4,5-dicarbomethoxy-2-phenylpyrrole

From the compound of Example 41 and benzaldehyde, yield, 78%, m.p. 218°–20° C. (from methanol).

EXAMPLE 49:
4-Acetyl-3-amino-1,5-dimethyl-2-phenylpyrrole (a) A solution of 1.4 g (0.00467 mole) of the compound of Example 46 in 25 ml of dimethylformamide is added dropwise to a cool suspension of sodium hydride in 10 ml of dimethylformamide. The resulting mixture is stirred at about 0°–5° C. for 15 minutes, then one ml of methyl iodide (0.0161 mole) is added. Stirring is continued for 30 minutes at about 0° C. and for 30 minutes at room temperature, then 150 ml of water is added to the reaction mixture, which is subsequently extracted with diethyl ether. The organic phase is separated and the solvent is evaporated off. The resulting residue (1.2 g) is recrystallized from isopropanol/water, m.p. 136°–38° C. It is the 4-acetyl-3-benzylideneamino-1,5-dimethyl-2-phenylpyrrole.

(b) 1.0 g (0.00316 mole) of the compound prepared in preceding (a) is dissolved in 30 ml of aqueous 10% hydrochloric acid and the resulting solution is heated at 80°–90° C. for about 2 hours. Upon cooling and neutralizing with sodium hydroxide, a precipitate forms which is recrystallized from ethanol/water; yield 0.8 g of the title compound, m.p. 124°–26° C.

The corresponding hydrochloride melts at 208°–9° C. (from ethanol/diethyl ether).

EXAMPLE 50:
4-Acetyl-3-amino-1-ethyl-5-methyl-2-phenylpyrrole

By procedure (a) of Example 49 and starting from the compound of Example 46 and ethyl iodide, the 4-acetyl-3-benzylideneamino-1-ethyl-5-methyl-2-phenylpyrrole is obtained, m.p. 139°–41° C. (from isopropanol/water). This compound is hydrolyzed as in procedure (b) of Example 49. Overall yield of the title compound: 54%, m.p. 107°–8° C. (from ethanol).

EXAMPLE 51:
4-Acetyl-3-amino-5-methyl-2-phenyl-1-propylpyrrole

Starting from the compound of Example 46 and propyl iodide, and using procedure (a) of Example 49, 4-acetyl-3-benzylideneamino-5-methyl-2-phenyl-1-propylpyrrole is obtained as an oily substance. This compound is hydrolyzed as in procedure (b) of Example 49. Yield of the title compound: 50%, m.p. 113°–15° C. (from ethanol).

EXAMPLE 52:
4-Acetyl-3-amino-1-(p-chlorobenzyl)-5-methyl-2-phenylpyrrole

The 4-acetyl-3-benzylideneamino-1-(p-chlorobenzyl)-5-methyl-2-phenylpyrrole is prepared from the compound of Example 46 and p-chlorobenzyl chloride by procedure (a) of Example 49, m.p. 136°–37° C. (from ethanol/water). This compound is hydrolyzed as in procedure (b) of Example 49. Yield of the title compound: 58%, m.p. 164°–66° C. (from ethanol/water).

EXAMPLE 53:
4-Acetyl-1-(o-chlorobenzyl)-5-methyl-3-dimethylamino-2-phenylpyrrole The title compound is prepared in a 67% yield by starting from the compound of Example 43 and o-chlorobenzyl chloride, using procedure (a) of Example 49; m.p. 103°–5° C. (from isopropanol).

EXAMPLE 54:
4-Acetyl-1(p-chlorobenzyl)-5-methyl-3-dimethylamino-2-phenylpyrrole The title compound is obtained in a 52% yield starting from the compound of Example 43 and p-chlorobenzyl chloride, by using procedure (a) of Example 49; m.p. 118°–19° C. (from hexane). The hydrochloride melts at 187°–88° C. (from water/ethanol).

EXAMPLE 55:
3-Amino-5-carbamoyl-4-carbomethoxy-2-phenylpyrrole

A solution of 5 g (0.0161 mole) of the compound of Example 41 is saturated with gaseous ammonia, then it is allowed to stand for two days. The title compound crystallizes and is recovered by filtration; yield 2.8 g, m.p. 177°–79° C. (from methanol/water).

What is claimed is:

1. A compound of the formula

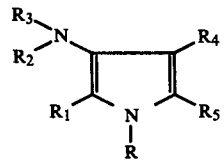

wherein:
R is selected from hydrogen, $(C_{1-4})$alkyl, benzyl and chlorobenzyl;
$R_1$ is selected from hydrogen, $(C_{1-4})$alkyl, phenyl and phenyl substituted by a radical selected from methyl, ethyl, methoxy, ethoxy, benzyloxy, fluoro, chloro and bromo;

$R_2$ and $R_3$ individually represent hydrogen, $(C_{1-4})$alkyl or, taken together, represent an isopropylidene, a benzylidene or a chlorobenzylidene radical;

$R_4$ is selected from carbo$(C_{1-3})$alkoxy; carbamoyl, methylcarbamoyl and phenylcarbamoyl;

$R_5$ represents carbo$(C_{1-3})$alkoxy or carbamoyl; or a salt thereof with a pharmaceutically-acceptable acid.

2. The compound of claim 1 which is 3-amino-4,5-dicarbomethoxy-2-(p-chlorophenyl)pyrrole hydrochloride.

3. The compound of claim 1 which is 3-amino-4,5-dicarbomethoxy-2-(p-tolyl)pyrrole hydrochloride.

4. The compound of claim 1 which is 3-amino-4,5-dicarboethoxy-2-phenylpyrrole hydrochloride.

5. The compound of claim 1 which is 3-amino-4,5-dicarbomethoxy-2-(p-methoxyphenyl)pyrrole hydrochloride.

6. The compound of claim 1 which is 3-amino-4,5-dicarbomethoxy-2-ethylpyrrole hydrochloride.

7. The compound of claim 1 which is 3-amino-4,5-dicarbomethoxy-2-phenylpyrrole hydrochloride.

8. The compound of claim 1 which is 3-amino-5-carbamoyl-4-carbomethoxy-2-phenylpyrrole.

* * * * *